(12) United States Patent
Suzuki

(10) Patent No.: US 6,218,517 B1
(45) Date of Patent: *Apr. 17, 2001

(54) PROTEIN HAVING A VASCULARIZATION INHIBITORY EFFECT AND A METHOD FOR PRODUCTION THEREOF AND A METHOD FOR PRODUCING ANGIOSTATIN

(75) Inventor: Kazuyasu Suzuki, Hamamatsu (JP)

(73) Assignee: Suzuki Motor Coporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/086,514

(22) Filed: May 28, 1998

(51) Int. Cl.$^7$ ............................... C07K 1/16; C07K 1/20; C07K 1/22
(52) U.S. Cl. ......................... 530/413; 530/412; 530/350
(58) Field of Search .................................. 530/413, 412, 530/350

(56) References Cited

FOREIGN PATENT DOCUMENTS 03000722    1/1991   (JP) .

OTHER PUBLICATIONS

Lewis Lung Carcinoma, "Angiostatin: A Novel Angiogenesis Inhibitor . . . ", Cell, vol. 79, 315–329 (1994).

James R. Powell et al., "Isolation of $Val_{3,5,4}$–Plasminogen as an Elastolytic . . . ," Biochemical And Biophysical Research Communications, vol. 102, No. 1, 45–62 (1981).

Francis J. Castellino, "Recent Advances in the chemistry of the Fibrinolytic System", Chemical Review, vol. 81, No. 5 (1981).

*Primary Examiner*—Michael Borin
(74) *Attorney, Agent, or Firm*—Burns, Doane, Swecker & Mathis, L.L.P.

(57) ABSTRACT

A protein derived from human plasminogen which has amino acids 355–791 of human plasminogen are purified. A method for purifying said protein and angiostatin comprises the steps of fractionating said protein by Lysine-Sepharose chromatography to separate plasminogen in Form 1 and Form 2 and applying separately each of them to a Lysine-Sepharose column in order.

1 Claim, 5 Drawing Sheets

FIG. 1 (RELATED ART)

AMINO ACID-PRIMARY STRUCTURE OF HUMAN PLASMINOGEN

→: INTRON, ◆: SUGAR CHAIN BINDING SITE,
↔: LIMITED DEGRADATION SITE WITH PLASMIN, PLASMINOGEN ACTIVATOR(PA), OR ELASTASE

H: ACTIVE SITE   K: KRINGLE

▼ : ELASTASE DEGRADATION
● : SUGAR CHAIN

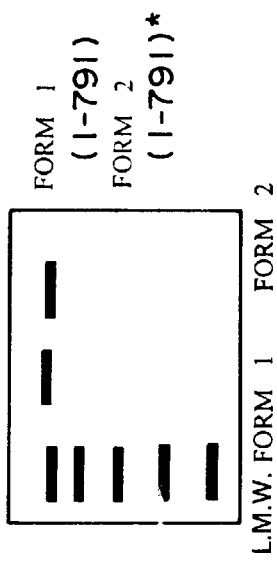
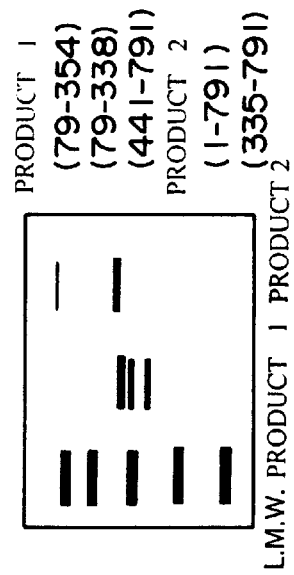
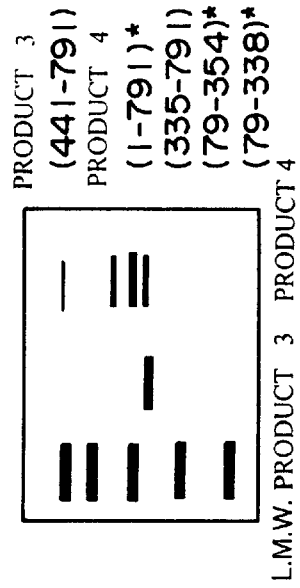
FIG. 4A   FIG. 4B   FIG. 4C
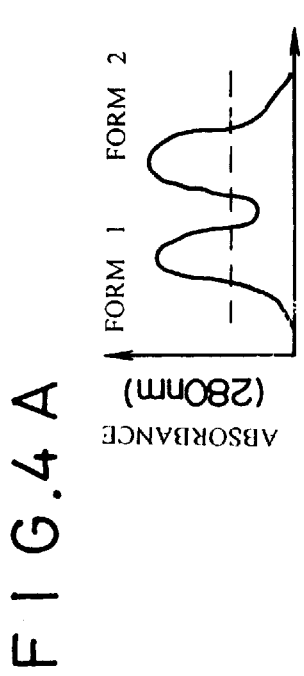
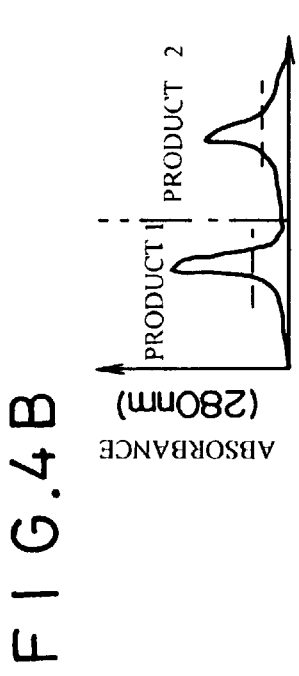
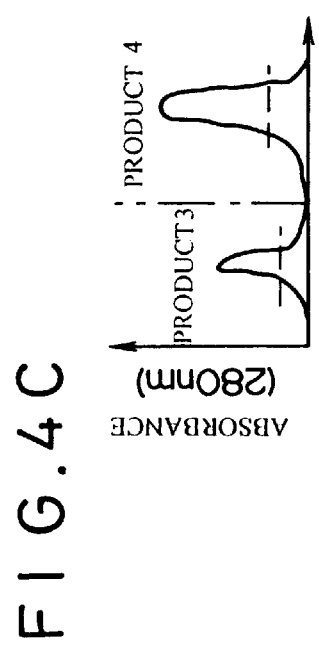

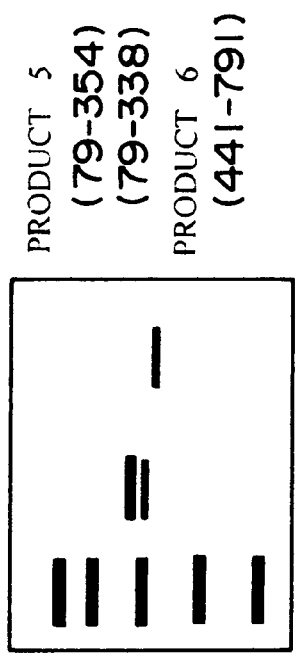
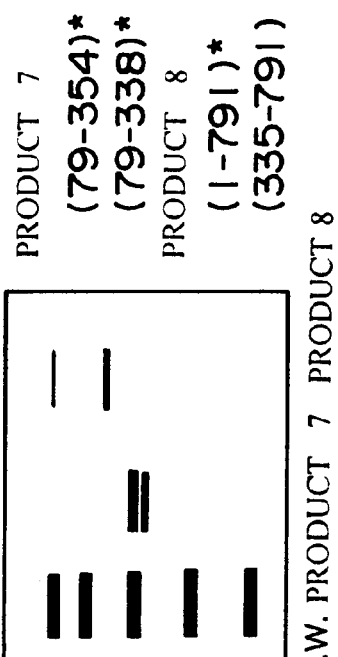
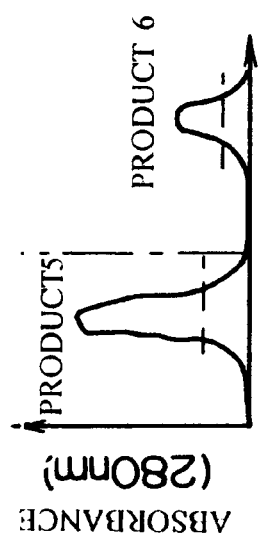
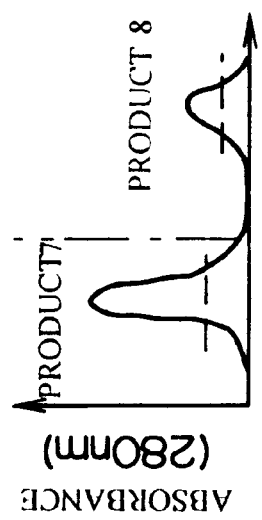
FIG. 5A
FIG. 5B

PROTEIN HAVING A VASCULARIZATION INHIBITORY EFFECT AND A METHOD FOR PRODUCTION THEREOF AND A METHOD FOR PRODUCING ANGIOSTATIN

TITLE OF THE INVENTION

A protein having a vascularization inhibitory effect and a method for production thereof and a method for producing angiostatin

BACKGROUND OF THE INVENTION

1. Field of the Invention

The present invention is related to vascularization inhibitors and a method for producing protein which is useful as a vascularization inhibitor.

2. Description of the Related Art

It is known in clinical field that, when a carcinoma is removed, other small tumors which were in a state of lull become activated to start growing or to raise their metastatic inclination. As a reason for this phenomena, the carcinoma itself is considered to produce some substances, which would inhibit the growth of other tumors. Angiostatin is known as one of such substances.

O'Reilley, et al. (Cell. Vol. 79, 315–328, Oct. 21, 1994, J. Folkman's Research Group) showed that urine and serum from mice having tumors inhibited metastasis of carcinoma in mice as well as growth of endothelial cells participating in vascularization. The substance showing such an inhibitory effect was purified and identified as a protein of 38 kDa by analysis of SDS-PAGE. This protein showed at least 98% homology to an internal fragment of 38 kDa plasminogen which fragment has N-terminal portion starting at mino acid 98 of plasminogen. (See the Discussion on the left column of page 323 of the above-mentioned reference.)

This protein called "angiostatin" has been found to coincides with a partial sequence of plasminogen. The plasminogen is a protein in plasma having 5 domains called "kringles". The kringle is a domain of triple loops formed by disulfide bonds. The domain is considered to play some role in linkages in which membranes, proteins and phospholipids are involved, and in regulating the proteolytic activity of enzymes. Hereinafter the five kringles will be referred to as "K1" to "K5" starting with K1 close to the N-terminus along the plasminogen molecule.

The structure of human plasminogen is shown in FIGS. 1–3. FIG. 1 is a partial modification of the figure on page 276 of "Hemostasis, Thrombus, Fibrinogenolysis", (Edited by Michio Matsuda, et al., p.276, First Edition published in 1994, Chugai-Igakusya Co. Tokyo, Japan). Plasminogen is a protein consisting of 791 amino acids and contains 5 kringles K1–K5. The amino acid sequence of plasminogen has been determined (FIG. 1). FIG. 1 shows this amino acid sequence, using one letter code. In FIG. 1, "A" means alanine, "C" means cysteine, "D" means asparagine acid, "E" means glutamic acid, "F" means phenylalanine, "G" means glycine, "H" means histidine, "I" means isoleucine, "K" means lysine, "L" means leucine, "M" means methionine, "N" means asparagine, "P" means proline, "Q" means glutamine, "R" means arginine, "S" means serine, "T" means threonine, "V" means valine, "W" means tryptophane, and "Y" means tyrosine. Human plasminogen has four an elastase hydrolytic sites. The peptide bonds at amino acids between position 78 and position 79, position 338 and position 339, position 354 and position 355, and position 440 and position 441 (or position 442 and position 443) can be hydrolyzed with an elastase. (These bonds are indicated by <—> in FIG. 1 and ▲ in FIGS. 2 and 3.)

Glycosylation sites exist at 289 and 346 amino acids of plasminogen (as shown by ♦ in FIG. 1, ● in FIG. 2 and ○ in FIG. 3). Plasminogen has two kinds of isoforms. One is attached to a sugar chain at amino acid 289 (Form 1), and the other has no sugar chain at amino acid 289 (Form 2).

Plasminogen has a lysine-binding site 1 in K1–K3 and another lysine-binding site 2 in K4 (marked by ☆ in FIG. 3), and so it can bind with lysine at these sites. In purifying plasminogen from plasma, Lysine-Sepharose chromatography can be used because of its property of binding with lysine. K5 has an aminohexal-binding site (marked by ◉ in FIG. 3).

The hydrolysis of human plasminogen with an elastase by O'Reilly, et al. was carried out under conditions so as to hydrolyze the peptide bonds at amino acids between positions 78 and 79, positions 338 and 339, positions 354 and 355, and positions 440 and 441 (or positions 442 and 443). Therefore, the resultant fragments are those from amino acids 1–78 (N-terminal potion of plasminogen), amino acids 79–338 (fragments containing K1–K3 considered to be a mixture of those derived from plasminogen in Form 1 and those derived from that in Form 2), amino acids 339–354 (a short fragment between K3 and K4), amino acids 355–440 (a fragment containing K4), and amino acids 441(or 443) –791 (the portion containing K5 and C-terminal portion of plasminogen, called "miniplasminogen").

Using the fragment containing K1–K3, the fragment containing K4 and miniplasminogen, O'Reilly, et al. carried out some experiments for the inhibitory effect on the growth of endothelial cells and on the metastasis of carcinoma. As the result, the inhibitory effects on the growth of endothelial cells and metastasis of carcinoma was observed only in the fragments containing K1–K3. On the contrary, no effect was observed either in the fragment containing K4 only or in human plasminogen itself.

O'Reilly, et al. named the fragments containing K1–K3 "purified angiostatin". Purified angiostatin is considered to inhibit the growth and metastasis of carcinoma cells by preventing vascularization.

Angiostatin can control the metastatic inclination of carcinoma, which would otherwise extremely increase after removal of the carcinoma, to the same level as before the carcinoma removal. In other words, the metastasis of carcinoma is inhibited after its removal by administering the same amount of angiostatin as produced by the carcinoma itself. Furthermore, angiostatin is obtained as a result of hydrolysis of plasminogen, which existing abundantly in the form of protein in plasma, as a substrate with an elastase which is a protease produced by vascular endothelial cells. As angiostatin itself is a protein existing in blood vessels, it is digested by a protease like plasmin. Therefore, it is considered that angiostatin can be used as an anticancer agent naturally occurring in a living body with almost no side effect. In addition, plasminogen is abundantly present in plasma, it is convenient to use plasminogen as a starting raw material for the production and purification of angiostatin. These suggest that angiostatin is excellent as one of known anti-metastatic agents.

In addition to angiostatin, fumagillin is also known as a vascularization inhibitor. Fumagillin is a kind of antibiotics produced by microorganisms that is different from angiostatin. Japanese Patent Publication No. 6-60095 discloses that fumagillin and its derivatives can be used as a vascularization inhibitor.

For using angiostatin as a carcinoma metastasis inhibitor, it is necessary to hydrolyze plasminogen extracted from plasma with an elastase and fractionate on columns. This fractionation can be presently effected only by HPLC. If angiostatin is to be extracted and purified according to such procedures, not only it is time-consuming and costly but also it shows low recovery. Besides, it is difficult to store angiostatin because of its strong inclination to decompose.

It is problematic to use fumagillin in clinical aspects because of its strong adverse side effects, though it is also effective like angiostatin in inhibiting vascularization and metastasis of carcinoma.

Moreover, it is disclosed in BBRC, Vol. 102, 1, 46–52, 1981 and Chemical Reviews, Vol. 81, Oct. 5, 1981 that the fragment consisting of amino acids 355–791 was obtained by limiting hydrolysis with an elastase. It is stated in the references that, after separating plasminogen into Form 1 and Form 2, the fragment bound on the Lysine-Sepharose column is eluted at gradient concentrations of -aminocaproic acid (hereinafter referred to as "EACA"), and that the several eluted peaks are further fractionated by gel filtration chromatography. However, the use of the gradient concentration of EACA and gel filtration chromatography as mentioned in the references is not suitable for recovering intermediate products like the fragment consisting of amino acids 355–791 of plasminogen, because these techniques need a longer time. Moreover, according to the references, the fragment consisting of the amino acids 355–791 is dealt with simply as an activated plasminogen but with no experiment to show any function of such fragments.

Therefore, there is a demand for a novel substance inhibiting vascularization with little adverse effects and a simple method of purifying angiostatin.

SUMMARY OF THE INVENTION

An object of the present invention is to provide a novel protein which is effective for inhibiting vascularization. In addition, another object is to provide a method for producing said protein and a simple method for purifying angiostatin with low cost.

Noticing that, of intermediate products obtained during the hydrolyzation of plasminogen, there may exist some substances which are more effective for inhibiting vascularization than purified angiostatin, the present inventors have investigated conditions for hydrolysis with an elastase and processes for purifying them. Thus, the present invention has been established.

Accordingly, the present invention provides a protein which is derived from human plasminogen and which has a sequence of amino acids 355–791 of human plasminogen.

In addition, the present invention provides a vascularization inhibitor comprising as an effective ingredient a protein which is derived from human plasminogen and which has a sequence of amino acids 355–791 of human plasminogen.

Further, the present invention provides a method for producing a protein which is derived from human plasminogen and which has a sequence of amino acids 355–791 of human plasminogen, said method comprising the steps of:

separating human plasminogen into Form 1 and Form 2 thereof by a first Lysine-Sepharose chromatography;

separately hydrolyzing each Form 1 and Form 2 of plasminogen with an elastase;

fractionating a hydrolyzate resulting from the above hydrolyzing step of the Form 1 of the plasminogen by a second Lysine-Sepharose chromatography;

collecting fractions bound on a Lysine-Sepharose column used in the second Lysine-Sepharose chromatography;

fractionating, by a third Lysine-Sepharose chromatography, a hydrolyzate resulting from the hydrolyzing step of the Form 2 of the plasminogen;

collecting fractions bound on a Lysine-Sepharose column used in the third Lysine-Sepharose chromatography;

further fractionating, by a Aminohexal-Sepharose chromatography, the fractions collected as a result of the third Lysine-Sepharose chromatography; and collecting fractions bound on an Aminohexal-Sepharose column of the Aminohexal-Sepharose chromatography.

Moreover, the present invention provides a method for producing a protein which is derived from human plasminogen and which has a sequence of amino acids 355–791 of human plasminogen, said method comprising the steps of:

separating human plasminogen into Form 1 and Form 2 thereof by a first Lysine-Sepharose chromatography;

hydrolyzing the separated Form 1 of plasminogen with an elastase;

fractionating, by a second Lysine-Sepharose chromatography, a hydrolyzate resulting from the above hydrolyzing step; and collecting fractions bound on a Lysine-Sepharose column used in the second Lysine-Sepharose chromatography.

The present invention provides a method for producing a protein which is derived from human plasminogen and which has a sequence of amino acids 355–791 of human plasminogen, said method comprising the steps of:

separating human plasminogen into Form 1 and Form 2 thereof by a first Lysine-Sepharose chromatography;

hydrolyzing the separated Form 2 of plasminogen with an elastase;

fractionating, by a second Lysine-Sepharose chromatography, a hydrolyzate resulting from the above hydrolyzing step;

collecting fractions bound on a Lysine-Sepharose column used in the second Lysine-Sepharose chromatography;

fractionating, by an Aminohexal-Sepharose chromatography, the fractions collected as a result of the second Lysine-Sepharose chromatography; and collecting fractions bound on an Aminohexal-Sepharose column of the Aminohexal-Sepharose chromatography.

The present invention provides a method for producing a protein which is derived from human plasminogen and which has a sequence of amino acids 355–791 of human plasminogen, said method comprising the steps of:

hydrolyzing human plasminogen with an elastase;

fractionating, by an Aminohexal-Sepharose chromatography, a hydrolyzate resulting from the above hydrolyzing step;

collecting fractions bound on an Aminohexal-Sepharose column used in the Aminohexal-Sepharose chromatography;

further fractionating, by a Lysine-Sepharose chromatography, the fractions collected as a result of the Aminohexal-Sepharose chromatography; and collecting fractions bound on a Lysine-Sepharose column of the Lysine-Sepharose chromatography.

In this process, human plasminogen can be previously separated into Form 1 and Form 2 thereof by a first Lysine-Sepharose chromatography, and each of the Form 1 and Form 2 can be separately hydrolyzed with an elastase and fractionated by an Aminohexal-Sepharose chromatography and then a second Lysine-Sepharose chromatography. Otherwise, it can be fractionated as it is without previous separation into Form 1 and Form 2 of human plasminogen.

Further, the present invention provides a protein produced in accordance with any one of the methods mentioned above.

The present invention provides a method for producing angiostatin, said method comprising the steps of:
- separating human plasminogen into Form 1 and Form 2 thereof by a first Lysine-Sepharose chromatography;
- separately hydrolyzing each of Form 1 and Form 2 of plasminogen with an elastase;
- fractionating, by a second Lysine-Sepharose chromatography, a hydrolyzate resulting from the above hydrolyzing step of the Form 1 of plasminogen;
- collecting fractions unbound on a Lysine-Sepharose column used in the second Lysine-Sepharose chromatography;
- further fractionating, by a first Aminohexal-Sepharose chromatography, the fractions collected as a result of the second Lysine-Sepharose chromatography;
- collecting fractions unbound on an Aminohexal-Sepharose column used in the first Aminohexal-Sepharose chromatography;
- fractionating, by a third Lysine-Sepharose chromatography, a hydrolyzate resulting from the above hydrolyzing step of the Form 2;
- collecting fractions bound on a Lysine-Sepharose column used in the third Lysine-Sepharose chromatography;
- fractionating, by a second Aminohexal-Sepharose chromatography, the fractions collected as a result of the third Lysine-Sepharose chromatography; and
- collecting fractions unbound on an Aminohexal-Sepharose column of the second Aminohexal-Sepharose chromatography.

The present invention provides a method for producing angiostatin, said method comprising the steps of:
- separating human plasminogen into Form 1 and Form 2 thereof by a first Lysine-Sepharose chromatography;
- hydrolyzing the separated Form 1 of plasminogen with an elastase;
- fractionating, by a second Lysine-Sepharose chromatography, a hydrolyzate resulting from the above hydrolyzing step of the Form 1 of the plasminogen;
- collecting fractions unbound on a Lysine-Sepharose column used in the second Lysine-Sepharose chromatography;
- fractionating, by an Aminohexal-Sepharose chromatography, the fractions collected as a result of the second Lysine-Sepharose chromatography; and
- collecting fractions unbound on an Aminohexal-Sepharose column of the Aminohexal-Sepharose chromatography.

The present invention provides a method for producing angiostatin, said method comprising the steps of:
- separating human plasminogen into Form 1 and Form 2 by a first Lysine-Sepharose chromatography;
- hydrolyzing the separated Form 2 of plasminogen with an elastase;
- fractionating, by a second Lysine-Sepharose chromatography, a hydrolyzate resulting from the above hydrolyzing step of Form 2 of the plasminogen;
- collecting fractions bound on a Lysine-Sepharose column used in the second Lysine-Sepharose chromatography;
- further fractionating, by an Aminohexal-Sepharose chromatography, the fractions collected as a result of the second Lysine-Sepharose chromatography; and
- collecting fractions unbound on an Aminohexal-Sepharose column of the Aminohexal-Sepharose chromatography.

The present invention provides a method for producing angiostatin, said method comprising the steps of:
- separating human plasminogen into Form 1 and Form 2 thereof by a first Lysine-Sepharose chromatography;
- separately hydrolyzing each of the separated Form 1 and Form 2 of plasminogen with an elastase;
- fractionating, by a first Aminohexal-Sepharose chromatography, a hydrolyzate resulting from the above hydrolyzing step of the Form 1 of plasminogen;
- collecting fractions unbound on an Aminohexal-Sepharose column used in the first Aminohexal-Sepharose chromatography;
- further fractionating, by a second Lysine-Sepharose chromatography, the fractions collected as a result of the first Aminohexal-Sepharose chromatography;
- collecting fractions unbound on a Lysine-Sepharose column of the second Lysine-Sepharose chromatography;
- fractionating, by a second Aminohexal-Sepharose chromatography, a hydrolyzate resulting from the above hydrolyzing step of the Form 2 of the plasminogen;
- collecting fractions unbound on an Aminohexal-Sepharose column used in the second Aminohexal-Sepharose chromatography;
- further fractionating, by a third Lysine-Sepharose chromatography, the fractions collected as a result of the second Aminohexal-Sepharose chromatography; and
- collecting fractions bound on a Lysine-Sepharose column of the third Lysine-Sepharose chromatography.

The present invention additionally is to provide angiostatin produced by the methods as described above.

BRIEF DESCRIPTION OF THE DRAWINGS

FIG. 1 is the structure of human plasminogen and its amino acid sequence, which is a partially modified drawing of "Hemostasis, Thrombus, Fibrinolysis" (Edited by Michio Matsuda, et al., p.276, First Edition in 1994, Chugai-Igakusya Co.).

FIGS. 4A–C are schematic view showing the elution curve and the result of SDS-PAGE in Example.

FIGS. 5A–B are schematic view showing the elution curve and the result of SDS-PAGE in Example.

DETAILED DESCRIPTION OF THE PREFERRED EMBODIMENT

Figure 2:
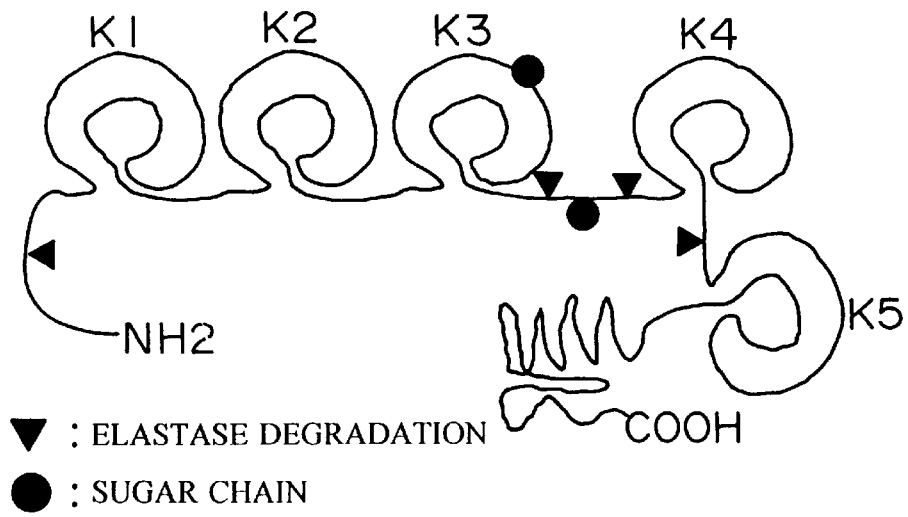
FIG. 2 is a schematic view showing the structure of human plasminogen.

The novel protein of the present invention is useful as a vascularization inhibitor, anticancer agent, antitumor agent, carcinoma metastatic inhibitor, carcinoma anti-metastatic agent, or carcinoma metastasis preventive because the protein is a metabolite of plasminogen broadly occurring in nature and shows vascularization inhibitory effect. Besides, according to the methods of the present invention, the novel protein above-mentioned and angiostatin can be produced more simply, more readily and at a lower cost than conventional methods. Moreover, it is possible to purify the angiostatin separately coming from Form 1 and Form 2 above.

For producing the protein showing a vascularization inhibitory effect and angiostatin coming from Form 1 and Form 2, at first plasminogen is extracted from plasma. For example, human plasminogen is purified by applying human plasma to a Lysine-Sepharose column. This human plasma can be used for purification, even if it has passed over the expiration date. Moreover, commercially available human plasminogen can be used.

Further, plasminogen is a precursor of plasmin which allows bulky fibrin to dissolve into serum. It is a protein broadly occurring in animal plasma. Depending upon animal species, the digestive sites of plasminogen with an elastase may vary, but it should be noted that the novel protein of the present invention and angiostatin can be purified from plasminogens coming from mammals other than humans according to the same producing methods as that described above by selecting appropriate combination of an elastase and plasminogens deriving from various animals.

The conditions for hydrolyzing plasminogen with an elastase are not specifically explained in the above-mentioned reference, Cell, Vol. 79, 315–328, Oct. 21, 1994. However, judging from the molecular weights of the resulting fragments, it is assumed that the hydrolysis of plasminogen with an elastase according to O'Reilly, et al. would have digested all sites to be hydrolyzed with an elastase as described in FIG. 1. (Refer to FIG. 9 of the reference.)

The protein of the present invention showing a vascularization inhibitory effect can be produced by obtaining an intermediary product prior to complete digestion and further purifying said product, because it is a product on the way to hydrolyze plasminogen.

For producing the objective product according to the present invention, it is convenient to change conventional conditions such as temperature, concentration of enzymes to be added or the like. Thus, appropriate intermediary hydrolyzates of plasminogen can be produced by combining one or more adjustments such as lowering the temperature or the conventional concentration of enzyme below that for conventional hydrolyzing conditions with an elastase.

For example, the hydrolysis is carried out by preparing several diluted solutions of an elastase with buffer to have different concentrations and adding them to plasminogen. Then, the molecular weight of the hydrolyzate is determined by SDS-PAGE, and a concentration of an elastase to induce hydrolysis only on the peptide bonds between amino acids 78 and 79, and amino acids 354 and 355 is determined. Hereinafter the hydrolysis will be carried out below that concentration.

Such a preferred concentration of an elastase is 0.2–20 $\mu$g/ml. At a concentration below 0.2 $\mu$g/ml, the hydrolysis may occur so slowly that it is practically ineffective. At a concentration more than 20 $\mu$g/ml, hydrolysis may occur in sites other than the objective sites. Preferable temperature for hydrolysis with an elastase is 20–45° C. At temperatures below 20° C. the hydrolysis may occur so slowly that it is practically ineffective. As temperatures higher than 45° C. the enzyme will be inactivated. Particularly preferable is 22–40° C. The hydrolysis with an elastase is carried out by appropriately combining said temperature with enzymatic concentration. Thus, appropriate adjustment is necessary, for example, the hydrolysis is effected by shortening the reaction time while controlling the temperature low, in case of at a higher enzymatic concentration. When the reaction time is set longer, the hydrolysis should be effected at lower temperatures with a lower enzymatic concentration. If an elastase is used, for example, at a reaction temperature of 25° C. with a concentration of 2 $\mu$g/ml for about 2 hours, the objective intermediary hydrolyzate is obtained. It can be confirmed by assaying the molecular weight by SDS-PAGE whether or not the objective intermediary hydrolyzate was obtained.

Figure 3:
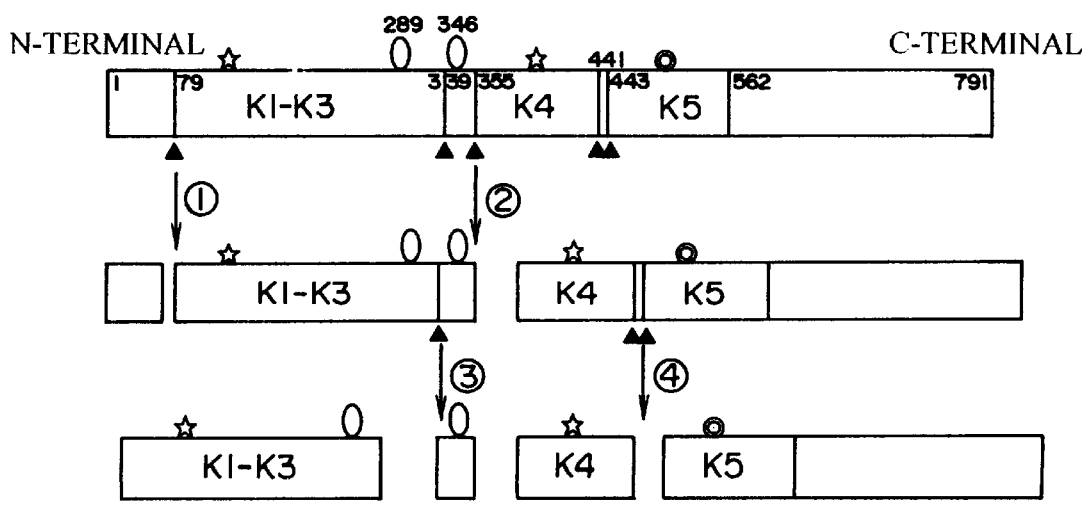
FIG. 3 is a schematic view showing the hydrolysis sites of human plasminogen with an elastase, glycosylation sites, lysine binding sites and aminohexal sites thereof.

The Hydrolysis of plasminogen with an elastase under the conditions above occurs on the peptide bond between amino acids 78–79 of plasminogen (marked by (1) in FIG. 3) and on the peptide bond between amino acids 354–355 thereof (marked by (2) in FIG. 3). The resultant fragments are different from the fragments of amino acids 1–78 (N-terminal portion of plasminogen), amino acids 79–354 (fragment containing K1–K3) and amino acids 355–791 (fragments containing K4 and miniplasminogen), respectively.

However, the hydrolysis occurs partially on the peptide bond between amino acids 338–339 (marked by (3) in FIG. 3) and on the peptide bond between amino acids 440–441 (marked by (4) in FIG. 3) (or on the peptide bond between amino acids 442–443), so that there are produced those fragments each consisting of amino acids 79–338 (fragments containing K1–K3), amino acids 339–354 (short fragment between K3 and K4), amino acids 355–440 (fragment containing K4) and amino acids 441(443)–791 (miniplasminogen), respectively.

The fragment containing K1–K3 includes two kinds coming from plasminogen in Form 1 and that in Form 2. The fragment coming from Form 1 is one attached to the sugar chain at 289 amino acid in the sequence, while the fragment coming from Form 2 is one without the sugar chain. According to the experiment by the present inventors, the fragment containing K1–K3 coming from plasminogen in Form 2 binds firmly to lysine, while the fragment containing K1–K3 and coming from plasminogen in Form 1 binds to lysine weakly.

When the hydrolyzate with an elastase under the conditions above is applied to a Lysine-Sepharose column, the column is binding to amino acids 79–354 (a fragment containing K1–K3 from Form 2) and amino acids 355–791 (a fragment containing K4 and miniplasminogen) as well as partially to amino acids 79–338 (a fragment of K1–K3 coming from Form 2), amino acids 355–440 (a fragment containing K4) and amino acids 79–791 (plasminogen).

The column is not binding to amino acids 1–78 (N-terminus of plasminogen) and amino acids 79–354 (a fragment of K1–K3 coming from Form 1). The column is also partially binding to amino acids 79–338 (a fragment of K1–K3 coming from Form 1), 441(443)–791 amino acids (miniplasminogen) and other small fragments. These fragments elute soon.

Such a method is unfavorable in view of productivity because the fragment containing K1–K3 has been included both in the fraction bound to the column and in the fraction unbound to the column.

Therefore, according to the method of the present invention, prior to the hydrolysis with an elastase, the plasminogen in Form 1 and Form 2 is fractionated by the Lysine-Sepharose chromatography while eluting with an increasing concentration of EACA. Thus, Form 1 is eluted at first, and subsequently Form 2 is eluted, whereby the plasminogen in Form 1 and Form 2 can be separated. A skilled person in the art would be able to select gradient concentrations of EACA. For example, Form 1 and Form 2 can be eluted with a gradient concentration of 2–12 mM.

Then, the plasminogen in Form 1 and Form 2 fractionated under the conditions above is hydrolyzed with an elastase and then further fractionated by the Lysine-Sepharose chromatography.

When the hydrolyzate of the plasminogen in Form 1 is applied to a Lysine-Sepharose column, the fragment consisting of amino acids 79–354 and partially those consisting of amino acids 79–338 and amino acids 441(443)–791 are found in fractions unbound to the column (hereinafter referred to as "Fraction 1"). The fragment consisting of amino acids 355–791 and in part those consisting of amino acids 355–440 and amino acids 79–791 are found in fractions bound to the column (hereinafter referred to as "Fraction 2").

When Fraction 4 is fractionated by the Aminohexal-Sepharose chromatography, the fragment consisting of amino acids 79–354 and in part those amino acids 355–440 and amino acids 79–338 are found in fractions unbound to the column (hereinafter referred to as "Fraction 7"). The fragment consisting of amino acids 355–791 and in part the fragment consisting of amino acids 79–791 are found in fractions bound to the column (hereinafter referred to as "Fraction 8").

Through the procedure as shown above, Fractions 2, 3 and 5–8 are obtained. In Fractions 2 and 8, the fragment containing K4 and miniplasminogen consisting of amino acids 355–791 are obtained. In Fraction 3 and 6, the miniplasminogen consisting of amino acids 441(443)–791 is mainly obtained. In Fraction 5, angiostatin coming from Form 1 and consisting of amino acids 79–354 is obtained, and in Fraction 7, angiostatin coming from Form 2 and consisting of amino acids 79–354 is obtained.

The fragments contained in each Fraction are summarized below in Table 1.

TABLE 1

| PLASMINOGEN | FRACTION | AMINO ACID SEQUENCE OF THE FRAGMENT | STRUCTURE CONTAINING THE FRAGMENT |
|---|---|---|---|
| FORM 1 | FRACTION 2 | amino acids 355–791 | K4 + MINIPLASMINOGEN |
|  |  | (amino acids 355–440) | K4 |
|  |  | (amino acids 79–791) | PLASMINOGEN |
|  | FRACTION 5 | amino acids 79–354 | K1–K3 |
|  |  | (amino acids 79–388) | K1–K3 |
|  | FRACTION 6 | (amino acids 441–791) | MINIPLASMINOGEN |
| FORM 2 | FRACTION 3 | (amino acids 441–791) | MINIPLASMINOGEN |
|  | FRACTION 7 | amino acids 79–354 | K1–K3 |
|  |  | (amino acids 79–338) | K1–K3 |
|  |  | (amino acids 355–440) | K4 |
|  | FRACTION 8 | amino acids 355–791 | K4 + MINIPLASMINOGEN |
|  |  | (amino acids 79–791) | PLASMINOGEN |

When the hydrolyzate of the plasminogen in Form 2 is similarly applied to a Lysine-Sepharose column, the fragment consisting of amino acids 441(443)–791 is found in fractions unbound to the column (hereinafter referred to as "Fraction 3"). The fragment consisting of amino acids 79–354, the fragment consisting of amino acids 355–791, and in part those consisting of amino acids 355–440, amino acids 79–338 and amino acids 79–791 are found in fractions bound to the column (hereinafter referred to as "Fraction 4").

Thus, the fragment consisting of amino acids 355–791 is included in Fractions 2 and 4, and angiostatin derived from plasminogen in Form 1 and Form 2 is included in Fractions 1 and 4, respectively.

Fractions 1 and 4 are further purified by fractionating with an Aminohexal-Sepharose column. Aminohexal-Sepharose can be binding to proteins containing aminohexal sites. Since plasminogen has an aminohexal site in K5, the fragment containing K5 can be bound to the aminohexal-Sepharose column.

When Fraction 1 is applied to the Aminohexal-Sepharose column, the fragment consisting of amino acids 79–354 and in part the fragment consisting of amino acids 79–338 are found in fractions unbound to the column (hereinafter referred to as "Fraction 5"). The fragment consisting of amino acids 441(443)–791 is found in fractions bound to the column (hereinafter referred to as "Fraction 6").

Further, plasminogen is hydrolyzed with an elastase in the same manner as above, and the hydrolyzate is applied to an Aminohexal-Sepharose column. Fractions bound to the column are collected and further fractionated by Lysine-Sepharose chromatography. The fragment consisting of amino acids 355–791 is contained in fractions bound to the Lysine-Sepharose column. In this case, plasminogen may previously be separated into Form 1 and Form 2 by Lysine-Sepharose chromatography, and then each of the separated plasminogen in Form 1 and Form 2 may be treated separately. Alternatively, the procedure may be carried out without separating into Form 1 and Form 2.

In addition, the plasminogen in Form 1 is hydrolyzed with an elastase in the same manner as above, and the hydrolyzate is applied to an Aminohexal-Sepharose column. Fractions unbound to the column are collected and further applied to a Lysine-Sepharose column. The fragment consisting of amino acids 79–354 is found in fractions unbound to the Lysine-Sepharose column. In the same manner as above, the plasminogen in Form 2 is hydrolyzed with an elastase, and the hydrolyzate is applied to an Aminohexal-Sepharose column. Fractions unbound to the column are collected and further applied to a Lysine-Sepharose column. The fragment consisting of amino acids 79–354 is found in fractions bound to the Lysine-Sepharose column.

Conventional techniques may be adopted for confirming the fragments, degree of purification and recoverability in each fraction. In particular, SDS-PAGE is suitable in view of its simple procedure.

Moreover, the vascularization inhibitory effect of the protein in the present invention derived from plasminogen can be confirmed by assaying the growth inhibitory potency of endothelial cells such as bovine capillary endothelial cells, bovine aortic endothelial cells, EOMA (mouse hemangioendothelioma), HUVEC (human umbilical vascular endothelial cells) and so on. It is also described in said reference, Cell, Vol. 79, 315–328, Oct. 21, 1994 that such growth inhibitory potency of endothelial cultured cells can reflect a vascularization inhibitory effect in vivo.

The protein fragment derived from plasminogen in the present invention can be administered to the subject by appropriate conventional means. For example, muscular injection, subcutaneous injection, intravascular injection, intraperitoneal injection, oral injection, nasal insufflation and the like are included in such known means. It may be collectively administered into appropriate organs through catheter or the like.

In general, a preferable dosage is about 0.01–10 mg/kg body weight by daily or at an interval of 2–5 days.

The protein derived from plasminogen in the present invention may be mixed with pharmaceutically acceptable carriers: for example, aqueous carriers such as sodium phosphate buffer or the like. It may be administered together with generally usable stabilizers, carbohydrates such as sorbitol, mannitol, starch, sucrose, dextrin, glucose or the like, proteins such as albumin, casein or the like, buffers such as alkali metal phosphate or the like.

The dosage and route of administration of the protein derived from plasminogen may be appropriately changed, depending upon route of administration, conditions of patients and so on.

The following examples are provided to illustrate the present invention, and should not be construed as limited thereof.

PURIFICATION OF PLASMINOGEN FROM HUMAN PLASMA

About 200 ml of human plasma stored under freezing was defrosted with water at 37° C., put in a dialyzer (cellulose tubing, 100 feet roll, size: 32/30, Sanko Junyaku K. K.) and dialyzed overnight at 4° C. against 4 L of water (20-fold volume). The ion strength of the plasma was lowered by the dialysis, and the protein having lysine binding sites was apt to be bound to a Lysine-Sepharose column. The plasma was centrifuged at 3000 rpm for 10 minutes, and the supernatant was recovered.

C1 complement was precipitated, and the precipitate was removed. The supernatant removed of C1 component was filtered. The filtrate was applied to a Lysine-Sepharose column. The Lysine-Sepharose column was prepared by reacting Sepharose 4B with lysine in the presence of CNBr and charging the resultant product into a column. Then, the column was washed with 200–300 ml of distilled water containing $1/1000$ volume of aprotinin until the absorbance at 280 nm of the eluted distilled water became below 0.05. Then, the column was washed with 200–300 ml of 0.2 M phosphate buffer (pH 7.4) containing $1/1000$ volume of aprotinin until the absorbance at 280 nm of the eluted phosphate buffer became below 0.05. Subsequently, the column was washed with 0.1 M phosphate buffer (pH 7.4) containing $1/1000$ volume of aprotinin and 0.2 M EACA to elute plasminogen bound to lysine, whereby fractions of plasminogen was obtained.

SEPARATION OF THE PLASMINOGEN IN FORM 1 AND FORM 2

The human plasminogen fractions purified by the method above were collected and subjected to dialysis for removing of 0.2 M EACA. About 20 ml of the plasminogen fraction was charged into a dialyzer (cellulose tubing, 100 feet roll, size: 32/30, Sanko Junyaku K. K.), and the dialysis was performed at 4° C. against 100-fold volume of 0.1 M phosphate buffer (pH 7.4). The dialysis was carried out by replacing twice the phosphate buffer, and one dialyzing time is 3 hours to one night.

After the dialysis, a filter (Centriflow, Pore Size 10,000, Amikon Corp.) was set on a centrifugal separator (for 1000 rpm), and the separation was performed at 1000 rpm for 20–30 minutes up to about ⅓ volume. Onto a column equilibrated with 0.1 M phosphate buffer (pH 7.4), the concentrated sample was applied to a Lysine-Sepharose column and then 0.1 M phosphate buffer was passed. The eluant was gradually substituted from 0.1 M phosphate buffer (pH 7.4) containing 2 mM of EACA to 0.1 M phosphate buffer (pH 7.4) containing 12 mM EACA so as to make a gradient concentration of EACA from 2–12 mM. When the absorbance at 280 nm was measured, two clear peaks were observed, and plasminogen in Form 1 was purified as first peak. The plasminogen in Form 2 was purified as second peak. FIG. 4A shows the elution curve and a typical drawing indicating the result of SDS-PAGE.

THE HYDROLYSIS OF PLASMINOGEN WITH AN ELASTASE

Into 1.5 ml tube was put a mixture consisting of 1000 μL of 5.2 μM plasminogen purified as above, 34.6 μL of 5000 KIE/ml aprotinin, 13.0 μL of 100×tranexamic acid, 260 μL of 0.5M phosphate buffer (pH 8.0) and 2 μg/ml of an elastase (human leukocyte elastase, Asterins Research Co., Purity 98%, Molecular Weight 29,500), and it was shaken for 2 hours in water at 25° C. The enzymatic reaction was allowed to stop on ice. After finishing the reaction, a part of the sample was used for measuring the molecular weight with SDS-PAGE, and it was confirmed that the hydrolysis was taken place on the peptide bond between amino acids 78 and 79 and between amino acids 354 and 355. To the rest of the sample was added 0.1 mM of PMSF, and the mixture was allowed to stand still for 10 minutes to complete the reaction.

FRACTIONATION OF THE FRAGMENT AFTER HYDROLYZING PLASMINOGEN IN FORM 1 WITH An ELASTASE

In the same manner as in separating plasminogen into Form 1 and Form 2 thereof, the fragments obtained by hydrolyzing plasminogen in Form 1 with an elastase were applied to another Lysine-Sepharose column. Each part of the fraction unbound to the column and the fraction bound to the column was used for confirming the molecular weight by SDS-PAGE. FIG. 4B shows the elution curve and a typical drawing indicating the result of SDS-PAGE.

The fractions unbound to the column included K1–K3 consisting of amino acids 79–354, and in part the fragment containing. K1–K3 consisting of amino acids 79–338, miniplasminogen consisting of amino acids 441(443)–791 and small fragments. These fractions unbound to the column are called "Product 1".

The fractions bound to the column included K4 consisting of amino acids 355–791 and miniplasminogen. Partially, plasminogen consisting of amino acids 79–791 and the fragment containing K4 consisting of amino acids 355–440 were contaminated, but the contaminants was found negligibly very few. These fractions bound to the column are called "Product 2".

FRACTIONATION OF THE FRAGMENT BY HYDROLYZING THE PLASMINOGEN IN FORM 2 WITH An ELASTASE

In the same manner as in the plasminogen in Form 1, the fragments obtained by hydrolyzing the plasminogen in Form 2 with an elastase were fractionated. Each part of the fraction unbound to the column and the fraction bound to the column was subjected to SDS-PAGE for confirming the molecular weight. FIG. 4C shows the elution curve and a typical drawing indicating the result of SDS-PAGE.

The miniplasminogen consisting of amino acids 441(443)–791 and in part small fragments were contained in the fractions unbound to the column. These fractions unbound to the column are called "Product 3".

The fragment containing K1–K3 consisting of amino acids 79–354 and the fragment containing K4 consisting of amino acids 355–791 and miniplasminogen were contained in the fractions bound to the column. In part, the fragment containing K1–K3 consisting of amino acids 79–338, plasminogen consisting of amino acids 79–791 and the fragment containing K4 consisting of amino acids 355–440 were contaminated, but the contaminants were negligibly few. These fractions bound to the column are called "Product 4".

FRACTIONATION OF PRODUCT 1 ON A COLUMN OF AMINOHEXAL-SEPHAROSE

Product 1 was further applied to an Aminohexal-Sepharose column. The Aminohexal-Sepharose column was prepared by reacting Sepharose 4B with 1,6-diaminohexane in the presence of CNBr and charging the resultant product into a column. Into the column equilibrated with Buffer 1 (0.1M phosphate buffer containing 0.1 M NaCl, pH 7.4), Product 1 was applied to the column and then Buffer 1 was added therein to collect the fractions unbound to the column. After confirming that the absorbance at 280 nm was lowered enough, the fractions bound to the column were eluted with Buffer 2 (0.1 M phosphate buffer containing 0.2 M EACA, pH 7.4). Each part of the fractions unbound to the column and the fractions bound to the column was subjected to SDS-PAGE for confirming the molecular weight. FIG. 5A shows the elution curve and a typical drawing indicating the result of SDS-PAGE.

The fragment containing K1–K3 consisting of amino acids 79–354 and in part the fragment containing K1–K3 consisting of amino acids 79–338 were included in the fractions unbound to the column. These fractions unbound to the column are called "Product 5".

The fractions bound to the column was miniplasminogen consisting of amino acids 441(443)–791. This fragment is called "Product 6".

FRACTIONATION OF PRODUCT 4 ON A COLUMN OF AMINOHEXAL-SEPHAROSE

Like Product 1, Product 4 was applied to an Aminohexal-Sepharose column. Each part of the fractions unbound to the column and the fractions bound to the column was subjected to SDS-PAGE for confirming the molecular weight. FIG. 5B shows the elution curve and a typical drawing indicating the result of SDS-PAGE.

The fragment containing K1–K3 consisting of amino acids 79–354 and in part the fragment containing K1–K3 consisting of amino acids 79–338 were in the fractions unbound to the column. These fractions unbound to the column are called "Product 7".

The fragment consisting of amino acids 355–791 and in part the fragment consisting of amino acids 79–791 were in the fractions bound to the column. These fragments are called "Product 8".

According to the following procedures, the following 4 kinds of products were mainly recovered.

Angiostatin derived from the plasminogen in Form 1 (hereinafter referred to as "Angiostatin 1"). This is a fragment containing K1–K3. The fragment consisting of amino acids 79–354 and in part the fragment consisting of amino acids 79–338 are contained in Angiostatin 1. Angiostatin 1 is contained in Product 5.

Angiostatin derived from the plasminogen in Form 2 (hereinafter referred to as "Angiostatin 2"). Like Angiostatin 1, this is a fragment containing K1–K3. The fragment consisting of amino acids 79–354 and in part the fragment consisting of amino acids 79–338 are contained in Angiostatin 2. Angiostatin 2 is contained in Product 7. Difference between Angiostatin 1 and Angiostatin 2 consists in having a sugar chain at the position 289 of plasminogen sequence.

Protein fragment consisting of K4 and miniplasminogen. This is the novel protein of the present invention. This is the fragment consisting of amino acids 355–791 of plasminogen. The protein derived from the plasminogen in Form 1 is the same as the protein derived from the plasminogen in Form 2. The substance consisting of K4 and miniplasminogen are contained in Products 2 and 8.

Miniplasminogen. This is the fragment consisting of amino acids 441(443)–791. The protein derived from the plasminogen in Form 1 is the same as the protein derived from the plasminogen in Form 2. Miniplasminogen is contained in Products 3 and 6.

CELL GROWTH ASSAY ACCORDING TO MTT METHOD

Inhibitory potency of said 4 Products (Product 5, Product 7, Products 2 and 8, Products 3 and 6) against the cell growth activity of human umbilicus vascular endothelial cells (HUVEC) was assayed by MTT method. Using MTT method, the cell growth potency is examined by measuring the absorbance at about 570 nm. As more the absorbance at about 570 nm, the higher the growth potency of the cell.

Previously, $7.5 \times 10^4$ cells of HUVEC (2nd generation, Kurabo Industries Ltd., Osaka Japan) were sowed in 25 cm$^2$ Culture Flask (Iwaki Corp.) containing 5 ml of EMG UV. EMG UV has a composition of modified MCDB131 medium, 2% bull serum, 10 $\mu$g/ml of endothelial growth factor (EGF), 1 $\mu$g/ml of hydrocortisone, 50 $\mu$g/ml of gentamycin, 0.25 $\mu$g/ml of amphotericin B, 10 $\mu$g/ml of heparin and 10 $\mu$g/ml of bovine brain extract. The culture mixture was incubated at 37° C. in 5% incubator until the culture became confluent. The medium was exchanged every other day, and a subculture kit manufactured by the same company was used.

To each well with 96-well plate were sowed about $2 \times 10^3$ cells (about $2 \times 10^4$ cells/ml) of HUVEC which had been almost confluent. Any one of 4 kinds of fractions above-mentioned was added, and the cultivation was maintained in the same manner as above for 4 days. Concentration of the fragment to be added were 0 $\mu$g/ml, 1.0 $\mu$g/ml, 2.5 $\mu$g/ml and 5.0 $\mu$g/ml in 4 occurrences.

Each 150 $\mu$l of medium was taken up from each well after the cultivation, and 100 $\mu$l of fresh medium which has previously been warmed in a CO$_2$ incubator was added thereto. Further, one hour cultivation was performed.

Figure 6:
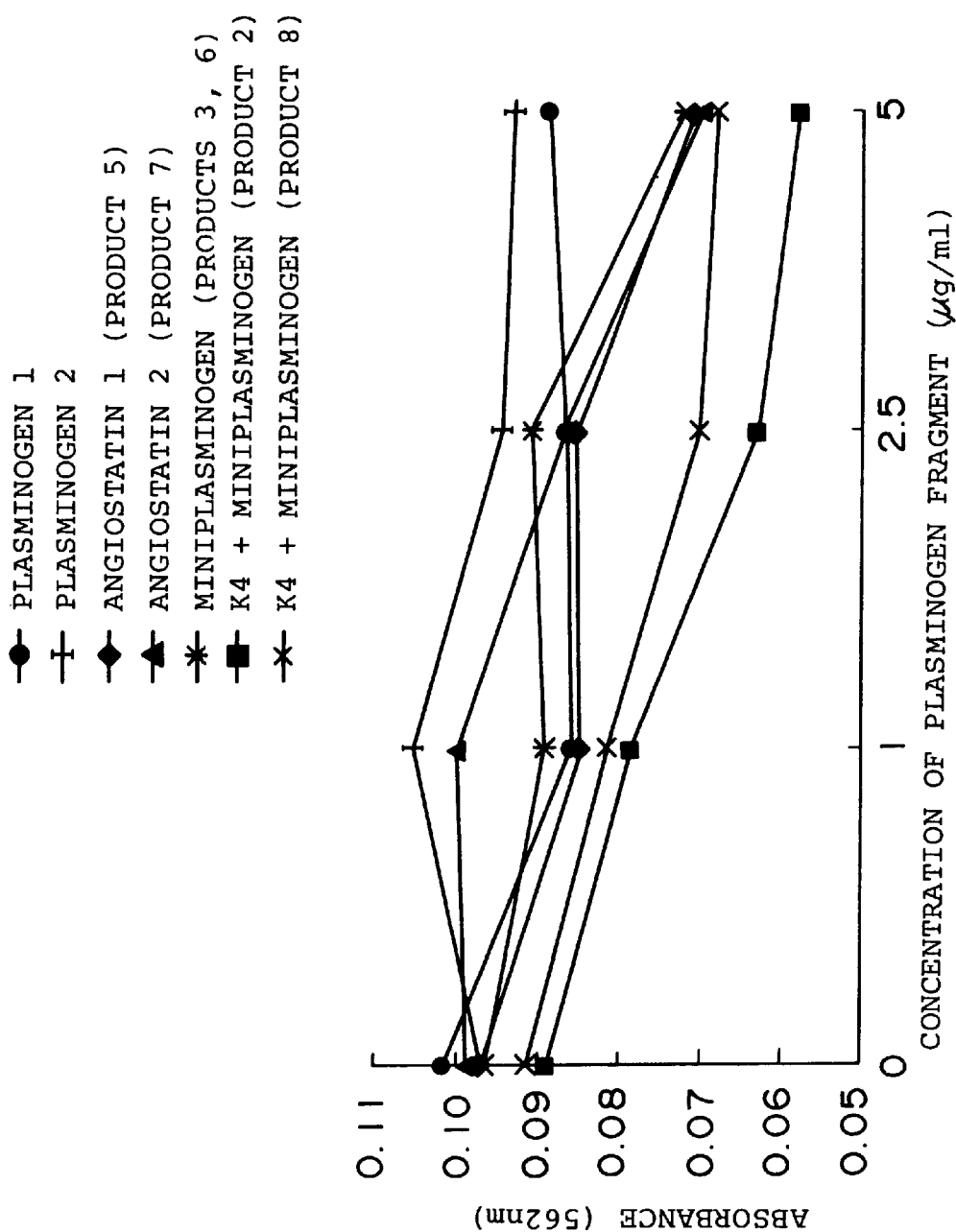
FIG. 6 is a graph showing the evaluation test of Product 5, Product 7, Products 2 and 8, and Products 3 and 6 obtained in Example according to MTT method.

Each 10 $\mu$l of A/B liquid previously prepared from MTT kit (50 mg MTT dried weight/vial, Chemicon International Inc.) was added to each well of 96-well plate after the cultivation. By hitting the side of the plate, A/B liquid was mixed well with the medium. After keeping warm in 5% CO$_2$ incubator for 4 hours, 100 $\mu$l of C liquid (developing liquid, isopropanol containing 0.04 N) was added to each well, and the mixture was stirred well with a micropipette. In reference to 660 nm of wavelength with microplate reader, the absorbance at 562 nm was measured. FIG. 6 shows the result. It means that the lower absorbance, the lower the growth potency of cell, and that the fragment to be added to the well showed high growth inhibitory effect.

The data demonstrates that the plasminogen both in Form 1 and Form 2 showed no growth inhibitory effect, and miniplasminogen from Product 3 and Product 6 was almost ineffective. Similarly to the result in O'Reilly et al, Angiostatin 1 from Product 7 and Angiostatin 2 from Product 5 showed growth inhibitory effect. Products 2 and 8 containing the novel substance of the present invention showed still a higher growth inhibitory effect than angiostatin. Product 2 includes the fragment containing K4 consisting of amino acids 355–440 and in part plasminogen consisting of amino acids 79–791 besides the substance of the present invention, but the contaminants were found to be negligibly few and these contaminants are known to be ineffective in the growth inhibitory effect from the result of O'Reilly, et al. experiments, so the growth inhibitory effect attained by this experiment was made by the novel substance consisting of amino acids 355–791 in the present invention. Likewise, the growth inhibitory effect as seen in Product 8 was attained by the novel substance consisting of amino acids 355–791 in the present invention.

Further, considering that HUVEC is adhesive cell with low cell growth ability, it is assumed that more clear data can be attained by multiplying several times the number of cells to be sowed.

According to the present invention, a novel substance which can inhibit the growth of endothelial cells is obtained.

The novel substance of the present invention can be easily fractionated from plasminogen abundantly contained in human plasma by means of affinity column chromatography only without needing expensive devices such as HPLC, FPLC or the like. Human plasma to be used as starting material is available at a low cost in a large scale, as it can be used even it passed over the expiration date. Further, according to the purification process of the present invention, angiostatin derived from the plasminogen in Form 1 (Angiostatin 1) and angiostatin derived from the plasminogen in Form 2 (Angiostatin 2) can be easily and separately purified respectively.

The novel substance of the present invention is a protein which can inhibit the growth of endothelial cells and shows vascularization inhibitory effect. In particular, the metastasis inclination remarkably elevated after removing tumor can be inhibited to the same level as before removing tumor. Moreover, the inhibitory effect is higher than angiostatin.

By utilizing said inhibitory effect, the novel substance of the present invention can be useful as vascularization inhibitor, anti-vascularization agent, anti-cancer metastatic agent or anticancer agent. The novel substance of the present invention seems to have no adverse side effects in using as medicine, since it is a protein occurring in nature as raw material that can be decomposed by protease or the like existing in a living body. Furthermore, it is favorable in a point of availability of raw material that the present substance can be available in a large scale, as described above.

What is claimed is:

1. A method for producing angiostatin, which is derived from human plasminogen and has sequence on amino acids 355–791 of human plasminogen, said method comprising the steps of:

separating human plasminogen into Form 1 and Form 2 thereof by a first Lysine-Sepharose chromatography;

separately hydrolyzing each of Form 1 and Form 2 of plasminogen with an elastase;

fractionating, by a second Lysine-Sepharose chromatography, a hydrolyzate resulting from the above hydrolyzing step of the Form 1 of plasminogen;

collecting fractions unbound on a Lysine-Sepharose column used in the second Lysine-Sepharose chromatography;

further fractionating, by a first Aminohexal-Sepharose chromatography, the fractions collected as a result of the second Lysine-Sepharose chromatography;

collecting fractions unbound on an Aminohexal-Sepharose column used in the first Aminohexal-Sepharose chromatography;

fractionating, by a third Lysine-Sepharose chromatography, a hydrolyzate resulting from the above hydrolyzing step of the Form 2;

collecting fractions bound on a Lysine-Sepharose column used in the third Lysine-Sepharose chromatography;

fractionating, by a second Aminohexal-Sepharose chromatography, the fractions collected as a result of the third Lysine-Sepharose chromatography; and collecting fractions unbound on an Aminohexal-Sepharose column of the second Aminohexal-Sepharose chromatography.

* * * * *

SEQUENCE LISTING

<160> NUMBER OF SEQ ID NOS: 1

<210> SEQ ID NO: 1
<211> LENGTH: 810
<212> TYPE: PRT
<213> ORGANISM: Human plasminogen
<220> FEATURE:
<221> NAME/KEY: SIGNAL
<222> LOCATION: (1)..(19)

<400> SEQUENCE: 1

```
Met Glu His Lys Glu Val Val Leu Leu Leu Leu Phe Leu Lys Ser
 1               5                  10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
        50                  55                  60

Gln Tyr His Ser Lys Glu Gln Gln Cys Val Ile Met Ala Glu Asn Arg
    65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
                100                 105                 110

Gly Thr Met Ser Lys Thr Lys Asn Gly Ile Thr Cys Gln Lys Trp Ser
            115                 120                 125

Ser Thr Ser Pro His Arg Pro Arg Phe Ser Pro Ala Thr His Pro Ser
```

```
           130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Cys Met His Cys Ser Gly Glu Asn
            180                 185                 190
Tyr Asp Gly Lys Ile Ser Lys Thr Met Ser Gly Leu Glu Cys Gln Ala
            195                 200                 205
Trp Asp Ser Gln Ser Pro His Ala His Gly Tyr Ile Pro Ser Lys Phe
        210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
            260                 265                 270
Tyr Gln Cys Leu Lys Gly Thr Gly Glu Asn Tyr Arg Gly Asn Val Ala
            275                 280                 285
Val Thr Val Ser Gly His Thr Cys Gln His Trp Ser Ala Gln Thr Pro
            290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys
            515                 520                 525
Asn Tyr Cys Arg Asn Pro Asp Gly Asp Val Gly Gly Pro Trp Cys Tyr
            530                 535                 540
Thr Thr Asn Pro Arg Lys Leu Tyr Asp Tyr Cys Asp Val Pro Gln Cys
545                 550                 555                 560
```

-continued

```
Ala Ala Pro Ser Phe Asp Cys Gly Lys Pro Gln Val Glu Pro Lys Lys
            565                 570                 575
Cys Pro Gly Arg Val Val Gly Gly Cys Val Ala His Pro His Ser Trp
            580                 585                 590
Pro Trp Gln Val Ser Leu Arg Thr Arg Phe Gly Met His Phe Cys Gly
        595                 600                 605
Gly Thr Leu Ile Ser Pro Glu Trp Val Leu Thr Ala Ala His Cys Leu
        610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Glu Ile Glu Val Ser Arg
            645                 650                 655
Leu Phe Leu Glu Pro Thr Arg Lys Asp Ile Ala Leu Leu Lys Leu Ser
            660                 665                 670
Ser Pro Ala Val Ile Thr Asp Lys Val Ile Pro Ala Cys Leu Pro Ser
        675                 680                 685
Pro Asn Tyr Val Val Ala Asp Arg Thr Glu Cys Phe Ile Thr Gly Trp
    690                 695                 700
Gly Glu Thr Gln Gly Thr Phe Gly Ala Gly Leu Leu Lys Glu Ala Gln
705                 710                 715                 720
Leu Pro Val Ile Glu Asn Lys Val Cys Asn Arg Tyr Glu Phe Leu Asn
                725                 730                 735
Gly Arg Val Gln Ser Thr Glu Leu Cys Ala Gly His Leu Ala Gly Gly
            740                 745                 750
Thr Asp Ser Cys Gln Gly Asp Ser Gly Gly Pro Leu Val Cys Phe Glu
            755                 760                 765
Lys Asp Lys Tyr Ile Leu Gln Gly Val Thr Ser Trp Gly Leu Gly Cys
    770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
                805                 810
```